United States Patent
Karavas et al.

(10) Patent No.: US 11,229,596 B2
(45) Date of Patent: Jan. 25, 2022

(54) PRESERVATIVE FREE PHARMACEUTICAL OPHTHALMIC COMPOSITIONS

(71) Applicant: PHARMATHEN S.A., Pallini Attikis (GR)

(72) Inventors: Evangelos Karavas, Pallini Attikis (GR); Efthymios Koutris, Pallini Attikis (GR); Vasiliki Samara, Pallini Attikis (GR); Ioanna Koutri, Pallini Attikis (GR); Anastasia Kalaskani, Pallini Attikis (GR); Andreas Kakouris, Pallini Attikis (GR); Manolis Fousteris, Pallini Attikis (GR)

(73) Assignee: PHARMATHEN S.A., Pallini Attikis (GR)

( * ) Notice: Subject to any disclaimer, the term of this patent is extended or adjusted under 35 U.S.C. 154(b) by 0 days.

(21) Appl. No.: 16/091,415

(22) PCT Filed: Apr. 11, 2017

(86) PCT No.: PCT/EP2017/025085
§ 371 (c)(1),
(2) Date: Oct. 4, 2018

(87) PCT Pub. No.: WO2017/182138
PCT Pub. Date: Oct. 26, 2017

(65) Prior Publication Data
US 2019/0117562 A1  Apr. 25, 2019

(30) Foreign Application Priority Data
Apr. 19, 2016 (GR) ................ 20160100175

(51) Int. Cl.
*A61K 9/00* (2006.01)
*A61K 47/34* (2017.01)
*A61K 31/5377* (2006.01)
*A61K 31/5575* (2006.01)
*A61K 47/44* (2017.01)

(52) U.S. Cl.
CPC ........ *A61K 9/0048* (2013.01); *A61K 31/5377* (2013.01); *A61K 31/5575* (2013.01); *A61K 47/34* (2013.01); *A61K 47/44* (2013.01)

(58) Field of Classification Search
CPC ...... A61K 9/0048; A61K 47/44; A61K 47/34; A61K 31/5377; A61K 31/5575
See application file for complete search history.

(56) References Cited

U.S. PATENT DOCUMENTS

| | | | |
|---|---|---|---|
| 8,999,938 B2* | 4/2015 | Horn | A61K 47/40 514/20.5 |
| 2004/0082660 A1 | 4/2004 | Ueno | |
| 2010/0210720 A1 | 8/2010 | Pilotaz et al. | |
| 2011/0028477 A1 | 2/2011 | Aleo et al. | |
| 2011/0105558 A1 | 5/2011 | Onishi et al. | |
| 2011/0319487 A1 | 12/2011 | Mercier | |
| 2013/0149394 A1 | 6/2013 | Takashima et al. | |
| 2014/0088107 A1* | 3/2014 | Swatscheck | A61K 9/0048 514/236.2 |
| 2014/0163030 A1 | 6/2014 | Aleo et al. | |
| 2014/0228364 A1 | 8/2014 | Hadj-Slimane | |

FOREIGN PATENT DOCUMENTS

| | | |
|---|---|---|
| EP | 2 127 638 A1 | 12/2009 |
| EP | 2 269 612 A1 | 1/2011 |
| EP | 2 567 689 A1 | 3/2013 |
| EP | 2 609 933 A1 | 7/2013 |
| WO | WO 2009/125246 A1 | 10/2009 |

OTHER PUBLICATIONS

International Search Report dated Jul. 31, 2017, in PCT/EP2017/025085, filed Apr. 11, 2017.
Haneda, M. et al., "Comparison of the Additive Effects of Nipradilol and Carteolol to Latanoprost in Open-Angle Glaucoma", Japanese Journal of Ophthalmology, vol. 50, No. 1, XP019375877, Jan. 1, 2006, pp. 33-37.
Third Party Observation filed May 25, 2021 in corresponding European Patent Application No. EP 17 725 511.4, 6 pages.
Office Action dated Aug. 25, 2021 in corresponding European Patent Application No. EP 17 725 511.4, 4 pages.

* cited by examiner

*Primary Examiner* — Sahar Javanmard
(74) *Attorney, Agent, or Firm* — Oblon, McClelland, Maier & Neustadt, L.L.P.

(57) ABSTRACT

The present invention relates to a preservative-free ophthalmic composition for the reduction of elevated intraocular pressure containing Latanoprost or a combination of Latanoprost and Timolol and to a process for preparing such compositions.

13 Claims, No Drawings

PRESERVATIVE FREE PHARMACEUTICAL OPHTHALMIC COMPOSITIONS

TECHNICAL FIELD OF THE INVENTION

The present invention relates to a preservative free ophthalmic aqueous composition for the reduction of elevated intraocular pressure containing a prostaglandin F2α analogue or a combination of a prostaglandin F2α analogue and a β-adrenergic receptor antagonist. Moreover, such preservative-free formulation is packed in container that ensures physical and chemical stability of the product.

BACKGROUND OF THE INVENTION

Glaucoma is a degenerative disease of the eye, wherein elevated intraocular pressure disrupts normal eye function and results in irreversible damage to the optic nerve head and loss of visual function. In particular, a glaucoma patient will develop peripheral visual field loss followed by central field loss usually in the presence of elevated intraocular pressure, which if left untreated it may eventually lead to blindness.

Most patients with glaucoma are treated with topical medication that controls elevated ocular pressure. Medications most commonly used are α-adrenergic receptor agonists, epinephrine compounds, prostaglandins that reduce ocular pressure by increasing aqueous outflow, β-adrenergic receptor antagonists and carbonic anhydrase inhibitors that work by decreasing aqueous production. Even though the typical treatment regimen for lowering intraocular pressure is topical β-blockers, in the recent years the use of prostaglandins as initial therapy is increased.

Prostaglandin F2α analogues in particular have been widely used for the treatment of glaucoma and ocular hypertension because of their effectiveness and their low systemic side effects. Most prostaglandin F2α analogues are described in U.S. Pat. Nos. 5,886,035, 5,807,892 and 6,096,783 and include Tafluprost, Travoprost, Latanoprost, Bimatoprost and others.

Latanoprost is a selective prostanoid FP receptor agonist which reduces intraocular pressure by increasing the outflow of aqueous humour. Reduction of the intraocular pressure in man starts about three to four hours after administration and maximum effect is reached after eight to twelve hours. Pressure reduction is maintained for at least 24 hours.

Latanoprost is colorless to pale yellowish viscous oil with a molecular weight of 432.59 and is practically insoluble in water, freely soluble in ethanol and very soluble in acetonitrile.

Almost all prostaglandin F2α analogues are practically insoluble in water. Thus, it is necessary to solve the problem of solubility in order to formulate them in suitable and stable ophthalmic solutions. EP-B-2178504 discloses addition of polyoxyl-15-hydroxystearate as solubilizer in prostaglandin ophthalmic solutions.

Another drug class commonly used for the treatment of ocular hypertension and glaucoma is the β-adrenergic receptor antagonists, also known as beta-blockers (b-blockers). This drug class was used in the treatment of angina, high blood pressure, abnormal heart rate and other such conditions; however, in recent years topical administration to the eye has shown that is successful in reducing intraocular pressure in patients with ocular hypertension and glaucoma.

Timolol maleate is a non-selective beta-blocker with many advantages compared to other glaucoma treatments. It shows longer duration of activity, minimal loss of effect throughout the duration of dosing and local anesthetic properties compared to other b-blockers. U.S. Pat. Nos. 4,195,085 and 4,861,760 describe the use of Timolol as an ophthalmic drug.

Timolol maleate is a white or almost white, odorless powder with a molecular weight of 432.5 and is soluble in water, ethanol and methanol, sparingly soluble in chloroform and propylene glycol and insoluble in ether and in cyclohexane.

In a large proportion of patients with ocular hypertension prostaglandins by themselves do not produce enough pressure reduction to reach the desired target. As a result, many such patients require more than one medication. As patient compliance is decreased when patient is required to administer separate medications for the treatment of a single condition, the present invention also provides fixed-dose combinations (FDCs) that include Latanoprost and Timolol combined in a single dosage form.

EP-A-2714007 discloses preservative free aqueous ophthalmic preparations comprising Latanoprost, Timolol and at least one polyvinyl alcohol.

There still remains a need for an effective and safe topical ophthalmic pharmaceutical composition containing Latanoprost or a combination of Latanoprost and Timolol with increased stability, improved solubility and fewer side effects. In particular, there is a need for an ophthalmic composition that is free from preservatives to be provided in a multiple use container and provide efficient dosing of the solution to the patient, without wastage.

SUMMARY OF THE INVENTION

The main objective of the present invention is to develop a stable, preservative-free ophthalmic formulation comprising Latanoprost or a combination of Latanoprost and Timolol to be used for the treatment of ocular hypertension providing a significant improvement over the prior art formulations.

It is an object of the present invention to provide an ophthalmic formulation that will overcome problems associated with the water-insolubility of the prostaglandin F2α analogues.

A further approach of the present invention is to provide ophthalmic solutions that are easily administrable in drop form.

A further object of the present invention is to provide a thermodynamically stable, preservative-free, aqueous pharmaceutical formulation comprising Latanoprost or a combination of Latanoprost and Timolol for ophthalmic use that effectively addresses issues related to ocular tolerability in glaucoma patients.

Moreover, an aspect of the present invention is to provide a preservative free ophthalmic formulation for topical administration containing Latanoprost or a combination of Latanoprost and Timolol which is bioavailable and with sufficient self-life.

Furthermore, it is an object of the present invention to provide an ophthalmic product that contains no antimicrobial preservatives, it is packed in a multi-dose container that maintains product sterility and is as effective in terms of therapy as products available with preservatives.

In accordance with the above objects of the present invention, a preservative-free pharmaceutical formulation for ophthalmic administration is provided comprising Latanoprost or a combination of Latanoprost and Timolol as the active ingredients and an effective amount of a solubilizing agent in order to provide adequate solubility.

According to another embodiment of the present invention, a process for the preparation of a preservative-free ophthalmic formulation containing Latanoprost or a combination of Latanoprost and Timolol and an effective amount of a solubilizing agent is provided and it consists of the following steps:

Adding successively in water for injection appropriate amounts of sodium chloride, sodium dihydrogen phosphate dihydrate, anhydrous disodium phosphate, disodium edetate dehydrate in some compositions and Timolol in case of FDC product to form Solution A.

Adding in water for injection appropriate amount of solubilizing agent and Latanoprost to form Solution B.

Mixing Solutions A and B.

Adjusting pH of the obtained solution to 6 by adding either sodium hydroxide or hydrochloric acid.

Adjusting to the final volume by adding water for injection and stirring until complete homogenization.

Adjusting pH again, if necessary, to 6 by adding either sodium hydroxide or hydrochloric acid.

Aseptic filling of the vials by a 0.22 μm sterilization filter membrane.

Other objects and advantages of the present invention will become apparent to those skilled in the art in view of the following detailed description.

DETAILED DESCRIPTION OF THE INVENTION

For the purpose of the present invention, a pharmaceutical composition comprising an active agent or a combination of active agents is considered "stable" if said agent or combination of agents degrades less of more slowly than it does on its own or in known pharmaceutical compositions.

Ocular administration of drugs is primarily associated with the need to treat ophthalmic diseases. Eye is the most easily accessible site for topical administration of a medication. Ophthalmic preparations are sterile products essentially free from foreign particles, suitably compounded and packaged for instillation into the eye. They are easily administered by the nurse or the patient himself, they have quick absorption and effect, less visual and systemic side effects, increased shelf life and better patient compliance.

Antimicrobial preservatives are added to aqueous preparations that are required to be sterile, such as in ophthalmic solutions. The use of preservatives in topical ophthalmic treatments is ubiquitous for any product that is to be used more than once by the patient as they prevent any microbes that may enter into the product after its first use from allowing those microbes to grow and infect the patient on a later use of the product. Although providing effective biocidal properties with well tolerated short-term use at low concentrations, preservatives can cause serious inflammatory effects on the eye with long-term use in chronic conditions, such as glaucoma or potentially ocular allergies.

Antimicrobial preservatives are not found in single use vials of ophthalmic solutions since they are manufactured aseptically or are sterilized and the products are used once and the dispenser is thrown away.

Preservative-free single dose containers most often are presented as blow-fill-seal (BFS) containers. The user takes the plastic vial and tears or cuts the plastic tip, inverts the vial and squeezes the ophthalmic liquid into the eye. Disadvantages of these systems are linked to the quite complicated filling technology, the need to overfill and amount of material needed for each dose. With an average drop size of ~35 μl and the standard commercial volume of 400-500 μl, five times the required drug quantity ends up being discarded in case of single dose containers. Additionally, a big amount of packaging material is required associated with high manufacturing costs. A further disadvantage is that, despite numerous technical improvements were made by some manufacturers, the edges around the tip of the opened dropper of disposable, single-dose container are still very sharp, which may cause an accident to the patients eye.

As the use of preservative containing eye drops has been implicated in the development or worsening of ocular surface disease, there is a tendency to limit their use by reducing their concentration as much as possible in eye drops. The present invention provides completely preservative-free ophthalmic formulations. Such formulations are packed in containers that enable to deliver preservative-free formulations while providing shelf life similar to traditional formulations. The containers of the present invention ensure that medication is kept germ-free even after multiple uses.

Patient compliance is greatly increased as the pumps of the present invention permit them to use preservative-free eye drops without worrying about the potential side effects caused by some preservatives and the related short- and long-term consequences, such as pain or discomfort, foreign body sensation, stinging or burning, dry eye sensation, ocular surface breakdown.

We have found that the design of the tip of the container produce a highly accurate drop size with low variability of drop volume between each drop dispensed.

Therefore, we present as a feature of the present invention a multi-use ophthalmic product comprising a container with an integral bacterial protection system and which has a dispensing tip, wherein the ratio of the inner to the outer diameter of the dispensing tip is from 1:1 to 1:6, and the container having an ophthalmic composition that is dispensed from the tip into the eye of a patient wherein the ophthalmic composition is a preservative-free aqueous solution and contains pharmaceutically acceptable excipients.

Tonicity plays an important role in successful administration of an aqueous solution and it refers to the osmotic pressure exerted by salts in the solution. A solution acceptable for ophthalmic administration is required to be isotonic to lacrimal fluid. Tonicity agents used can be selected from, but are not limited to, sodium chloride, mannitol, dextrose, glycerin, potassium chloride, calcium chloride, magnesium chloride, propylene glycol and glycerol. Sodium chloride is the preferred tonicity agent in the present invention. In order to be produced isotonic solutions sodium chloride content should be no more than 0.9%. The ophthalmic composition according to the present invention comprises sodium chloride in the range 0.25% to 0.50% (w/v).

Ophthalmic solutions are ordinarily buffered at a pH that ensures maximum stability for the drugs they contain. The buffers are included to minimize any change in pH during storage which will affect the stability and solubility of the drug. pH in the range of 5.8 to 6.2 is considered optimum for ophthalmic solutions of the present invention. More preferably pH is adjusted to 6. Suitable buffering agents include, but are not limited to, sodium dihydrogen phosphate dihydrate, anhydrous disodium phosphate, hydrochloric acid, sodium hydroxide, sodium hydrogen carbonate.

Chelating agents are a class of coordination or complex compounds consisting of a central metal atom attached to a large molecule in a cyclic or ring structure. Disodium edetate dehydrate (EDTA) is a calcium chelator, mainly active on the tight junctions between epithelial cells, whose integrity seems to be dependent on $Ca^{+2}$. It is known to produce ultra-structural changes in the corneal epithelium, resulting in decrease of the overall lipophilic characteristics of this tissue and in expansion of intercellular spaces. These physiological alternations of corneal epithelium or endothelium are correlated with changes in corneal hydration and with drug permeability through the cornea. The ophthalmic composition according to the present invention comprises disodium edetate dehydrate up to 0.15% (w/v).

Solubilizing agents are used to improve solubility of poorly water-soluble drugs such as prostaglandin F2α analogues. Solubilizing agents can be selected from, but are not limited to, polyoxyl 40 hydrogenated castor oil (Cremophor RH-40), polyoxyl 35 castor oil (Cremophor EL), poloxamer 407, polysorbate 20, benzalkonium chloride, cyclodextrins, lecithin, benzyl alcohol, benzyl benzoate.

The hydrophilic-lipophilic balance (HLB) of a solubilizing agent is a measure of the degree to which it is hydrophilic or lipophilic, determined by calculating values for the different regions of the molecule. Solubilizing agents with HLB>10 are used in the present invention. Cremophor RH-40, Cremophor EL, polysorbate 20 and poloxamer 407 are preferably used in the present invention due to their high HLB value. More preferably, Cremophor RH-40, Cremophor EL and poloxamer 407 are used in the present invention.

It has been unexpectedly found that when certain quantities of solubilizing agents are included in aqueous preservative-free ophthalmic preparations of Latanoprost either alone or in combination with Timolol, the dosage form exhibits adequate solubility and bioavailability. The present invention comprises either a castor oil derivative, i.e Cremophor RH-40 or Cremophor EL in an amount of 1.5%-5% (w/v) or a combination of Cremophor RH 40 with Poloxamer 407. Poloxamer 407 is comprised in an amount of 1.5%-3% (w/v).

Solutions intended for ophthalmic use must be sterile. Dry heat, steam under pressure and gas sterilization are common sterilization techniques; however, they might result in degradation of the active ingredient. Therefore, sterilization via aseptic filtration is the method preferred in the present invention. Several types of filter are available including hydrophilic polyvinylidene fluoride, hydrophilic modified polyvinylidene fluoride, polyethersulfone, double polyethersulfone, hydrophilic modified polyethersulfone, hydrophilic polytetrafluoroethylene, N66 posidyne, nylon. 0.22 μm hydrophilic modified polyvinylidene fluoride (PVDF) filter is preferred in the present invention.

The manufacturing process followed in all formulations of the present invention is described below:

Preparation of Solution A

In a clean vessel of appropriate size the 70% of water for injection is added.

The appropriate amount of sodium chloride is dispensed to the vessel under stirring until dissolution.

The appropriate amount of sodium dihydrogen phosphate dihydrate is dispensed to the vessel under stirring until dissolution.

The appropriate amount of anhydrous disodium phosphate is dispensed to the vessel under stirring until dissolution.

The appropriate amount of disodium edetate dehydrate is dispensed to the vessel under stirring until dissolution (in compositions where a chelating agent is present).

The appropriate amount of Timolol maleate is dispensed to the vessel under stirring until dissolution (in case of FDC product).

Preparation of Solution B

In a separate clean vessel of appropriate size the 10% of water for injection is added.

The appropriate amount of solubilizing agent and/or co-solubilizing agent is dispensed to the vessel under stirring until dissolution.

The appropriate amount of Latanoprost is dispensed to the above vessel and the solution is stirred until complete dissolution.

Preparation of Final Solution

The solution B is transferred quantitatively into the preparation vessel of solution A and the mixture is stirred until complete homogenization.

The vessel of solution B is rinsed twice with water for injection and all the rinses are added into the final mixture.

The pH of the solution is adjusted to 6.00 (if necessary) by adding either sodium hydroxide or hydrochloric acid of 0.1N or 1N.

The solution volume is adjusted to the final volume by adding water for injections and the solution is stirred until complete homogenization.

The pH of the solution is checked again and it is adjusted to 6.00 (if necessary) by adding either sodium hydroxide or hydrochloric acid of 0.1N or 1N.

Aseptic filling of the vials by a 0.22 μm sterilization filter membrane.

EXAMPLES

In the examples below different solubilizing agents were tested.

At the beginning of formulation development, the current invention focuses on an ophthalmic preparation containing Cremophor RH-40 as a solubilizing agent. The main function of Cremophor RH-40 in the solution is the micellization, the formation of micelles entrapping the drug molecules in the center. Along the micellization, the hydrophobic core of Cremophor RH-40 encloses drug molecules.

Alternative Cremophor RH-40 contents were applied in the current invention in order to figure out the impact of Cremophor RH-40 content on a) the drug-excipient micellization and b) the product's stability profile.

TABLE 1

Compositions 1-5 of Latanoprost

| | Compositions | | | | |
|---|---|---|---|---|---|
| | 1 | 2 | 3 | 4 | 5 |
| | % w/v | | | | |
| Latanoprost | 0.005 | 0.005 | 0.005 | 0.005 | 0.005 |
| Cremophor RH-40 | 0.250 | 0.500 | 1.500 | 2.500 | 5.000 |
| NaCl | 0.410 | 0.400 | 0.400 | 0.400 | 0.400 |
| $NaH_2PO_4 \cdot 2H_2O$ | 0.900 | 0.900 | 0.885 | 0.885 | 0.680 |
| $Na_2HPO_4$ | 0.170 | 0.160 | 0.160 | 0.160 | 0.120 |
| NaOH/HCl 1N | q.s pH 6.00 | | | | |
| Water for injections | q.s 100.0 | | | | |

TABLE 2

Compositions 1-5 of Latanoprost-Timolol

| | Compositions | | | | |
|---|---|---|---|---|---|
| | 1 | 2 | 3 | 4 | 5 |
| | % w/v | | | | |
| Latanoprost | 0.005 | 0.005 | 0.005 | 0.005 | 0.005 |
| Timolol | 0.500 | 0.500 | 0.500 | 0.500 | 0.500 |
| Timolol Maleate | 0.683 | 0.683 | 0.683 | 0.683 | 0.683 |
| Cremophor RH-40 | 0.250 | 0.500 | 1.500 | 2.500 | 5.000 |
| NaCl | 0.410 | 0.400 | 0.380 | 0.360 | 0.320 |
| $NaH_2PO_4 \cdot 2H_2O$ | 0.720 | 0.720 | 0.720 | 0.720 | 0.720 |
| $Na_2HPO_4$ | 0.300 | 0.300 | 0.300 | 0.300 | 0.300 |
| NaOH/HCl 1N | q.s pH 6.00 | | | | |
| Water for injections | q.s 100.0 | | | | |

The physicochemical properties and assay of Compositions 1-5 are presented in table 3 & 4 below.

TABLE 3

Physicochemical properties and assay of Compositions 1-5 of Latanoprost

| | 1 | 2 | 3 | 4 | 5 |
|---|---|---|---|---|---|
| pH | 6.02 | 6.03 | 6.05 | 6.02 | 6.03 |
| Osmolality (mOsmol/kg) | 268 | 255 | 267 | 258 | 266 |
| Surface tension (mN/m) | 47.36 | 46.59 | 45.49 | 44.12 | 43.92 |
| Viscosity (cP) - 100 rpm, spindle 00 | 1.34 | 1.36 | 1.38 | 1.39 | 1.44 |
| Specific gravity | 1.010 | 1.009 | 1.011 | 1.011 | 1.012 |
| Appearance | Clear, Colorless solution | | | | |
| Assay Latanoprost | 99.3% | 99.9% | 99.7% | 101.1% | 98.6% |

TABLE 4

Physicochemical properties and assay of Compositions 1-5 of Latanoprost-Timolol

| | 1 | 2 | 3 | 4 | 5 |
|---|---|---|---|---|---|
| pH | 6.05 | 6.00 | 6.03 | 6.03 | 6.05 |
| Osmolality (mOsmol/kg) | 289 | 294 | 295 | 296 | 292 |
| Surface tension (mN/m) | 47.36 | 46.78 | 45.49 | 44.17 | 43.64 |
| Viscosity (cP) - 100 rpm, spindle 00 | 1.39 | 1.40 | 1.38 | 1.39 | 1.44 |
| Specific gravity | 1.012 | 1.012 | 1.012 | 1.013 | 1.013 |
| Appearance | Clear, Colorless solution | | | | |
| Assay Latanoprost | 98.2% | 99.9% | 99.1% | 100.5% | 99.2% |

According to the results, the higher the Cremophor RH-40 content, the lower the surface tension of the solution. It is known in the literature that the surface tension of a solution changes strongly with the concentration of the surfactant. As long as the content of Cremophor RH-40 gets increased, more micelles are formed into the aqueous solution resulting in the strong entrapment of drug molecules. Upon introduction of Cremophor RH-40 into the system, they will initially partition into the interface. The system free energy is reduced by lowering the energy of the interface (calculated as area times surface tension), and removing the hydrophobic parts of the surfactant from contact with water.

Subsequently, when the surface coverage by the Cremophor RH-40 increases, the surface free energy (surface tension) decreases and the surfactant starts aggregating into micelles, thus again decreasing the system's free energy by decreasing the contact area of hydrophobic parts of the surfactant with water.

Taking into account the screening study on Cremophor RH-40, compositions of Cremophor RH-40 with content higher than 1.5% w/v are preferred.

On the next step, formulation development focuses on Cremophor EL.

TABLE 5

Compositions 6-8 of Latanoprost

| | Compositions | | |
|---|---|---|---|
| | 6 | 7 | 8 |
| | % w/v | | |
| Latanoprost | 0.005 | 0.005 | 0.005 |
| Cremophor EL | 0.500 | 2.500 | 5.000 |
| NaCl | 0.548 | 0.470 | 0.420 |
| $NaH_2PO_4 \cdot 2H_2O$ | 0.620 | 0.620 | 0.620 |
| $Na_2HPO_4$ | 0.100 | 0.100 | 0.100 |
| NaOH/HCl 1N | q.s pH 6.00 | | |
| Water for injections | q.s 100.0 | | |

TABLE 6

Compositions 6-8 of Latanoprost-Timolol

| | Compositions | | |
|---|---|---|---|
| | 6 | 7 | 8 |
| | % w/v | | |
| Latanoprost | 0.005 | 0.005 | 0.005 |
| Timolol | 0.500 | 0.500 | 0.500 |
| Timolol Maleate | 0.683 | 0.683 | 0.683 |
| Cremophor EL | 0.500 | 2.500 | 5.000 |
| NaCl | 0.400 | 0.360 | 0.320 |
| $NaH_2PO_4 \cdot 2H_2O$ | 0.720 | 0.720 | 0.720 |
| $Na_2HPO_4$ | 0.300 | 0.300 | 0.300 |
| NaOH/HCl 1N | q.s pH 6.00 | | |
| Water for injections | q.s 100.0 | | |

The physicochemical properties and assay of Compositions 6-8 are presented in table 7 & 8 below.

TABLE 7

Physicochemical properties and assay of Compositions 6-8 of Latanoprost

| | 6 | 7 | 8 |
|---|---|---|---|
| pH | 6.02 | 6.04 | 6.04 |
| Osmolality (mOsmol/kg) | 265 | 262 | 259 |
| Surface tension (mN/m) | 45.05 | 44.38 | 43.93 |
| Viscosity (cP) - 100 rpm, spindle 00 | 1.37 | 1.40 | 1.44 |
| Specific gravity | 1.009 | 1.010 | 1.010 |
| Appearance | Clear, Colorless solution | | |
| Assay Latanoprost | 99.1% | 98.9% | 99.6% |

TABLE 8

Physicochemical properties and assay of Compositions 6-8 of Latanoprost-Timolol

| | 6 | 7 | 8 |
|---|---|---|---|
| pH | 6.02 | 6.04 | 6.03 |
| Osmolality (mOsmol/kg) | 294 | 296 | 292 |
| Surface tension (mN/m) | 46.16 | 44.36 | 43.49 |

TABLE 8-continued

Physicochemical properties and assay of
Compositions 6-8 of Latanoprost-Timolol

|  | 6 | 7 | 8 |
|---|---|---|---|
| Viscosity (cP) - 100 rpm, spindle 00 | 1.39 | 1.40 | 1.44 |
| Specific gravity | 1.012 | 1.012 | 1.013 |
| Appearance | Clear, Colorless solution | | |
| Assay Latanoprost | 98.5% | 99.0% | 99.3% |

It is obvious that the higher the Cremophor EL content, the lower the surface tension of the solution. Taking into account the screening study on Cremophor EL, compositions of Cremophor EL with content higher than 2.5% w/v are preferred.

Apart from castor oil derivatives (Cremophor EL & RH-40), formulation development also focuses on alternative solubilizing agents. Poloxamer 407 is applied either as the only surfactant in the solution or in combination with Cremophor RH-40 (Table 9 & 10). The development focuses on the combination of solubilizing agents as the key proposition on surface tension decrease.

TABLE 9

Compositions 9-12 of Latanoprost

| | Compositions | | | |
|---|---|---|---|---|
| | 9 | 10 | 11 | 12 |
| | % w/v | | | |
| Latanoprost | 0.005 | 0.005 | 0.005 | 0.005 |
| Cremophor RH-40 | — | — | 1.500 | 2.500 |
| Poloxamer 407 | 0.200 | 1.500 | 1.500 | 1.500 |
| NaCl | 0.540 | 0.380 | 0.387 | 0.300 |
| $NaH_2PO_4 \cdot 2H_2O$ | 0.620 | 0.890 | 0.867 | 0.885 |
| $Na_2HPO_4$ | 0.105 | 0.160 | 0.160 | 0.160 |
| NaOH/HCl 1N | q.s pH 6.00 | | | |
| Water for injections | q.s 100.0 | | | |

TABLE 10

Compositions 9-12 of Latanoprost-Timolol

| | Compositions | | | |
|---|---|---|---|---|
| | 9 | 10 | 11 | 12 |
| | % w/v | | | |
| Latanoprost | 0.005 | 0.005 | 0.005 | 0.005 |
| Timolol | 0.500 | 0.500 | 0.500 | 0.500 |
| Timolol Maleate | 0.683 | 0.683 | 0.683 | 0.683 |
| Cremophor RH-40 | — | — | 1.500 | 2.500 |
| Poloxamer 407 | 0.200 | 1.500 | 1.500 | 1.500 |
| NaCl | 0.500 | 0.400 | 0.340 | 0.340 |
| $NaH_2PO_4 \cdot 2H_2O$ | 0.680 | 0.680 | 0.680 | 0.680 |
| $Na_2HPO_4$ | 0.250 | 0.250 | 0.240 | 0.240 |
| NaOH/HCl 1N | q.s pH 6.00 | | | |
| Water for injections | q.s 100.0 | | | |

The physicochemical properties and assay of Compositions 9-12 are presented in table 11 & 12 below.

TABLE 11

Physicochemical properties and assay
of Compositions 9-12 of Latanoprost

| | 9 | 10 | 11 | 12 |
|---|---|---|---|---|
| pH | 6.02 | 6.08 | 6.07 | 6.03 |
| Osmolality (mOsmol/kg) | 261 | 264 | 267 | 261 |
| Surface tension (mN/m) | 47.25 | 39.85 | 42.81 | 41.46 |
| Viscosity (cP) - 100 rpm, spindle 00 | 1.34 | 1.38 | 1.52 | 1.64 |
| Specific gravity | 1.009 | 1.011 | 1.012 | 1.013 |
| Appearance | Clear, Colorless solution | | | |
| Assay Latanoprost | 99.5% | 98.6% | 98.9% | 98.4% |

TABLE 12

Physicochemical properties and assay of
Compositions 9-12 of Latanoprost-Timolol

| | 9 | 10 | 11 | 12 |
|---|---|---|---|---|
| pH | 6.03 | 6.02 | 6.05 | 6.03 |
| Osmolality (mOsmol/kg) | 294 | 292 | 293 | 292 |
| Surface tension (mN/m) | 47.02 | 39.23 | 42.35 | 41.73 |
| Viscosity (cP) - 100 rpm, spindle 00 | 1.36 | 1.38 | 1.55 | 1.66 |
| Specific gravity | 1.012 | 1.012 | 1.013 | 1.014 |
| Appearance | Clear, Colorless solution | | | |
| Assay Latanoprost | 99.0% | 99.5% | 99.2% | 98.9% |

According to the results poloxamer 407 1.5% w/v is preferred. The synergies developed between Cremophor RH-40 and poloxamer 407 decrease effectively the surface tension comparing to compositions comprising solely Cremophor RH-40. This can be explained by the increased formation of synergistic micelles into the solution which entrap drug molecules resulting to an extended decrease of surface free energy of the system.

Similarly, formulation development focuses on compositions comprising polysorbate 20 either solely as a solubilizing agent or in combination with Cremophor RH-40.

TABLE 13

Compositions 13-15 of Latanoprost

| | Compositions | | |
|---|---|---|---|
| | 13 | 14 | 15 |
| | % w/v | | |
| Latanoprost | 0.005 | 0.005 | 0.005 |
| Cremophor RH-40 | — | — | 2.500 |
| Polysorbate 20 | 0.050 | 1.000 | 1.000 |
| NaCl | 0.530 | 0.510 | 0.370 |
| $NaH_2PO_4 \cdot 2H_2O$ | 0.620 | 0.620 | 0.885 |
| $Na_2HPO_4$ | 0.100 | 0.100 | 0.160 |
| NaOH/HCl 1N | q.s pH 6.00 | | |
| Water for injections | q.s 100.0 | | |

TABLE 14

Compositions 13-15 of Latanoprost-Timolol

| | Compositions | | |
|---|---|---|---|
| | 13 | 14 | 15 |
| | % w/v | | |
| Latanoprost | 0.005 | 0.005 | 0.005 |
| Timolol | 0.500 | 0.500 | 0.500 |

TABLE 14-continued

Compositions 13-15 of Latanoprost-Timolol

| | Compositions | | |
|---|---|---|---|
| | 13 | 14 | 15 |
| | % w/v | | |
| Timolol Maleate | 0.683 | 0.683 | 0.683 |
| Cremophor RH-40 | — | — | 2.500 |
| Polysorbate 20 | 0.050 | 1.000 | 1.000 |
| NaCl | 0.500 | 0.400 | 0.360 |
| $NaH_2PO_4 \cdot 2H_2O$ | 0.680 | 0.680 | 0.730 |
| $Na_2HPO_4$ | 0.200 | 0.200 | 0.260 |
| NaOH/HCl 1N | q.s pH 6.00 | | |
| Water for injections | q.s 100.0 | | |

The physicochemical properties and assay of Compositions 13-15 are presented in table 15 & 16 below.

TABLE 15

Physicochemical properties and assay of Compositions 13-15 of Latanoprost

| | 13 | 14 | 15 |
|---|---|---|---|
| pH | 6.00 | 6.00 | 6.04 |
| Osmolality (mOsmol/kg) | 265 | 258 | 262 |
| Surface tension (mN/m) | 43.20 | 39.94 | 42.77 |
| Viscosity (cP) - 100 rpm, spindle 00 | 1.36 | 1.40 | 1.37 |
| Specific gravity | 1.008 | 1.008 | 1.012 |
| Appearance | Clear, Colorless solution | | |
| Assay Latanoprost | 98.5% | 99.6% | 99.2% |

TABLE 16

Physicochemical properties and assay of Compositions 13-15 of Latanoprost-Timolol

| | 13 | 14 | 15 |
|---|---|---|---|
| pH | 6.02 | 6.04 | 6.03 |
| Osmolality (mOsmol/kg) | 295 | 296 | 292 |
| Surface tension (mN/m) | 43.40 | 41.64 | 42.77 |
| Viscosity (cP) - 100 rpm, spindle 00 | 1.38 | 1.40 | 1.48 |
| Specific gravity | 1.008 | 1.012 | 1.013 |
| Appearance | Clear, Colorless solution | | |
| Assay Latanoprost | 98.5% | 99.1% | 99.0% |

According to the results, polysorbate 20 1% w/v is preferred. Similarly to Cremophor RH-40, the higher the polysorbate 20 content, the higher the micelles formation into the solution, the lower the free energy system. The synergies developed between Cremophor RH-40 and polysorbate 20 decrease effectively the surface tension comparing to compositions comprising solely Cremophor RH-40. This can be explained by the increased formation of synergistic micelles into the solution which entrap drug molecules resulting to an extended decrease of surface free energy of the system.

Similarly, formulation development focuses on formula comprising disodium edetate dehydrate in combination with Cremophor RH-40.

TABLE 17

Composition 16 of Latanoprost

| | Composition 16 % w/v |
|---|---|
| Latanoprost | 0.005 |
| Cremophor RH-40 | 2.500 |
| Disodium edetate dehydrate | 0.111 |
| NaCl | 0.370 |
| $NaH_2PO_4 \cdot 2H_2O$ | 0.900 |
| $Na_2HPO_4$ | 0.130 |
| NaOH/HCl 1N | q.s pH 6.00 |
| Water for injections | q.s 100.0 |

TABLE 18

Composition 16 of Latanoprost-Timolol

| | Composition 16 % w/v |
|---|---|
| Latanoprost | 0.005 |
| Timolol | 0.500 |
| Timolol Maleate | 0.683 |
| Cremophor RH-40 | 2.500 |
| Disodium edetate dehydrate | 0.111 |
| NaCl | 0.360 |
| $NaH_2PO_4 \cdot 2H_2O$ | 0.800 |
| $Na_2HPO_4$ | 0.250 |
| NaOH/HCl 1N | q.s pH 6.00 |
| Water for injections | q.s 100.0 |

The physicochemical properties and assay of Compositions 16 are presented in table 19 & 20 below.

TABLE 19

Physicochemical properties and assay of Composition 16 of Latanoprost

| | 16 |
|---|---|
| pH | 6.02 |
| Osmolality (mOsmol/kg) | 263 |
| Surface tension (mN/m) | 45.73 |
| Viscosity (cP) - 100 rpm, spindle 00 | 1.40 |
| Specific gravity | 1.010 |
| Appearance | Clear, Colorless solution |
| Assay Latanoprost | 99.5% |

TABLE 20

Physicochemical properties and assay of Composition 16 of Latanoprost-Timolol

| | 16 |
|---|---|
| pH | 6.02 |
| Osmolality (mOsmol/kg) | 293 |
| Surface tension (mN/m) | 44.89 |
| Viscosity (cP) - 100 rpm, spindle 00 | 1.39 |
| Specific gravity | 1.013 |
| Appearance | Clear, Colorless solution |
| Assay Latanoprost | 99.2% |

According to the results, disodium edetate dehydrate/ Cremophor RH-40 2.5% w/v formulation (Composition 16) has similar physicochemical properties with the Cremophor RH-40 2.5% formulation (Composition 4). The chelating agent is expected to enhance the drug permeability on the corneal epithelium while preventing the discomfort caused by benzalkonium chloride. Also, the expansion of intercellular spaces instead of disruption of the epithelial membrane integrity in the case of benzalkonium Chloride, exhibits the benefits of EDTA as an alternative drug permeability enhancer.

It is already known in the literature that the stabilization mechanism of Latanoprost is the micelle formation. The surfactants form micelles upon dispensing in the solution and they inhibit the adsorption to eye drop containers as well as the Latanoprost hydrolysis. It is common that the hydrolysis of Latanoprost is accompanied by the production of Latanoprost acid.

According to the formulation development, the stability profile of compositions 1, 3, 4, 5, 7, 10, 12, 14 and 16 is examined. The device is a multi-dose PF container dispensing drops while maintaining sterility and constant drop volume. The containers are loaded into stability chambers and monitored with an HPLC method. The containers are pre-sterilized and meet specifications of pharmacopeia.

Stability data of optimized formulation upon storage at zero time, 3 and 6 months under refrigerator (5° C.±3° C.), long term (25° C./60% RH), intermediate (30° C./60% RH) and accelerated storage conditions (40° C./75% RH) are presented in tables 21 & 22.

TABLE 21

Stability results of Compositions 1, 3, 4, 5, 7, 10, 12, 14, 16 of Latanoprost

| Latanoprost ASSAY (%) | Zero time | 3 months | | | | 6 months | | | |
|---|---|---|---|---|---|---|---|---|---|
| | | 5° C. | 25° C. | 30° C. | 40° C. | 5° C. | 25° C. | 30° C. | 40° C. |
| 1 | 100.4 | 98.1 | 98.4 | 97.3 | 93.2 | 96.5 | 93.2 | 93.2 | 86.2 |
| 3 | 101.8 | 102.2 | 99.7 | 99.9 | 100.4 | 99.4 | 98.2 | 97.8 | 91.3 |
| 4 | 102.2 | 101.8 | 101.3 | 100.6 | 100.9 | 101.2 | 100.8 | 100.2 | 99.8 |
| 5 | 99.3 | 99.1 | 98.6 | 98.5 | 97.9 | 98.4 | 98.2 | 98.4 | 98.3 |
| 7 | 103.0 | 101.6 | 100.8 | 99.2 | 98.9 | 103.2 | 102.9 | 99.9 | 97.6 |
| 10 | 97.8 | 93.9 | 94.2 | 93.2 | 42.5 | 89.9 | 91.0 | 29.3 | 5.1 |
| 12 | 99.0 | 98.9 | 98.9 | 99.0 | 97.6 | 98.8 | 98.4 | 98.1 | 97.2 |
| 14 | 99.2 | 99.8 | 98.2 | 97.8 | 93.2 | 98.9 | 97.6 | 94.0 | 75.6 |
| 16 | 99.5 | 99.7 | 99.8 | 99 | 98.9 | 99.4 | 98.7 | 98.5 | 98.2 |

TABLE 22

Stability results of Compositions 1, 3, 4, 5, 7, 10, 12, 14, 16 of Latanoprost-Timolol

| | Zero time | 3 months | | | | 6 months | | | |
|---|---|---|---|---|---|---|---|---|---|
| | | 5° C. | 25° C. | 30° C. | 40° C. | 5° C. | 25° C. | 30° C. | 40° C. |
| Latanoprost ASSAY (%) | | | | | | | | | |
| 1 | 100.6 | 99.1 | 98.4 | 97.2 | 94.6 | 97.0 | 94.1 | 93.8 | 88.5 |
| 3 | 101.6 | 99.7 | 99.8 | 99.2 | 98.6 | 98.9 | 98.1 | 97.6 | 92.0 |
| 4 | 101.1 | 100.1 | 99.6 | 99.5 | 99.2 | 99.9 | 100.2 | 99.1 | 98.9 |
| 5 | 102.5 | 103.2 | 101.8 | 102.0 | 100.1 | 102.0 | 102.3 | 101.7 | 99.6 |
| 7 | 102.8 | 103.5 | 103.1 | 101.9 | 101.0 | 102.4 | 102.0 | 101.1 | 99.7 |
| 10 | 99.8 | 97.1 | 96.8 | 96.4 | 58.7 | 91.2 | 90.7 | 48.7 | 27.1 |
| 12 | 98.9 | 99.3 | 99.2 | 99.0 | 99.1 | 99.3 | 99.5 | 98.5 | 98.3 |
| 14 | 99.8 | 100.3 | 98.9 | 98.2 | 97.3 | 99.3 | 98.0 | 97.7 | 82.3 |
| 16 | 99.2 | 99.3 | 99.0 | 99.0 | 99.1 | 98.7 | 98.6 | 98.2 | 98.1 |
| Timolol ASSAY (%) | | | | | | | | | |
| 1 | 99.7 | 100.1 | 99.4 | 99.1 | 99.2 | 99.2 | 99.4 | 99.0 | 98.7 |
| 3 | 100.8 | 100.2 | 100.0 | 100.3 | 99.8 | 99.8 | 100.3 | 99.2 | 99.3 |
| 4 | 99.2 | 99.5 | 99.9 | 98.7 | 98.4 | 100.1 | 99.5 | 98.8 | 98.4 |
| 5 | 100.3 | 99.7 | 100.0 | 99.2 | 99.3 | 100.5 | 99.0 | 99.4 | 98.5 |
| 7 | 101.5 | 101.3 | 101.2 | 102.6 | 101.3 | 101.3 | 101.2 | 101.8 | 102.8 |
| 10 | 102.0 | 101.5 | 101.0 | 102.5 | 101.4 | 100.9 | 101.9 | 102.0 | 101.7 |
| 12 | 100.9 | 100.4 | 100.2 | 100.6 | 100.1 | 100.3 | 100.5 | 100.8 | 100.3 |
| 14 | 101.4 | 101.3 | 101.2 | 101.3 | 102.3 | 102.9 | 103.2 | 102.8 | 101.8 |
| 16 | 101.9 | 100.9 | 101.3 | 101.2 | 103.0 | 101.2 | 101.4 | 102.8 | 100.5 |

According to the stability data the higher Cremophor RH-40 content enhances the chemical stability of pharmaceutical prostaglandin formulation by micelle formation mechanism. Cremophor RH-40 contents higher than 1.5% are indicated for the stabilization of Latanoprost since the stability profile of composition is stable even under accelerated (40° C./75% RH) storage conditions. Neither polysorbate 20 nor poloxamer 407 can stabilize the prostaglandin compositions since the Latanoprost assay decreases in all storage conditions. The micelles of these surfactants aren't strong enough to inhibit either the Latanoprost adsorption to the container or its hydrolysis. On the contrary, the combination of Cremophor RH-40 2.5% and poloxamer 407 1.5% (Composition 12) as well as the combination of Cremophor RH-40 2.5% and disodium edetate dehydrate (Composition 16) stabilize the composition since the Latanoprost assay is constant even under accelerated storage conditions.

Based on the physicochemical properties and the stability profile of the current compositions the optimized formula may comprise a castor oil derivative as solubilizing agent (e.g. Cremophor EL or Cremophor RH-40) or a combination of Cremophor RH-40 with poloxamer 407 or a combination of Cremophor RH-40 with disodium edetate dehydrate.

In order to ensure that the filter used during the manufacturing process does not retain the drug substance Latanoprost and does not cause impurities to the final product, a filter study was performed. The procedure simulated the production filtration, by using different filter membranes. Samples of the solution before and after filtration were collected and were analyzed under assay and impurities method determination. Totally, four membrane materials, Hydrophilic modified PVDF, PTFE, Polyethersulphone-PES and Nylon were tested.

Before filtration 5 portions of 2 ml each were selected from the solution and the mixture sample was analyzed for Assay and Related substances. After filtration of each filter membrane, 5 portions of 2 ml were selected from the solution and the mixture sample was analyzed for Assay and related substances determination. The results of the filter study are presented in tables 23 & 24 below.

Acceptance Criteria:

The % Assay of API after filtration should be between ±2% of Assay before filtration.

The % difference in Total impurities after filtration should be not more than 5% compared to the Total impurities before filtration.

TABLE 23

Results of filter study for Latanoprost

Before Filtration

Assay

| Sample | % Assay Latanoprost |
|---|---|
| Average Before | 98.8% |

Impurities

| SPECIFICATIONS (LIMIT) | % Impurities Before Filtration |
|---|---|
| Total Impurities % Latanoprost (NMT 6.0%) | 0.08% |

TABLE 23-continued

Results of filter study for Latanoprost

After filtration

Assay

| Sample | % Assay | | | |
|---|---|---|---|---|
| | Filter 1 PVDF | Filter 2 PES | Filter 3 PTFE (Hydrophilic) | Filter 4 NYLON |
| Latanoprost Assay % | 98.7% | 97.9% | 98.6% | 98.5% |

Impurities

| SPECIFICATIONS (LIMIT) | % Impurities | | | |
|---|---|---|---|---|
| | Filter 1 PVDF | Filter 2 PES | Filter 3 PTFE (Hydrophilic) | Filter 4 NYLON |
| Total Impurities % Latanoprost (NMT 6.0%) | 0.08% | 0.08% | 0.09% | 0.08% |

TABLE 24

Results of filter study for Latanoprost-Timolol

Before Filtration

Assay

| Sample | % Assay Latanoprost | % Assay Timolol |
|---|---|---|
| Average Before | 100.4% | 95.3% |

Impurities

| SPECIFICATIONS (LIMIT) | % Impurities Before Filtration |
|---|---|
| Total Impurities % Latanoprost (NMT 6.0%) | 0.05% |
| Total Impurities % Timolol (NMT 3.0%) | 0.01% |

After filtration

Assay

| Sample | % Assay | | | |
|---|---|---|---|---|
| | Filter 1 PVDF | Filter 2 PES | Filter 3 PTFE (Hydrophilic) | Filter 4 NYLON |
| Latanoprost Assay % | 100.6% | 100.4% | 101.0% | 101.0% |
| Timolol Assay % | 95.5% | 95.5% | 96.2% | 95.6% |

Impurities

| SPECIFICATIONS (LIMIT) | % Impurities | | | |
|---|---|---|---|---|
| | Filter 1 PVDF | Filter 2 PES | Filter 3 PTFE (Hydrophilic) | Filter 4 NYLON |
| Total Impurities % Latanoprost (NMT 6.0%) | 0.09% | 0.08% | 0.09% | 0.11% |
| Total Impurities % Timolol (NMT 3.0%) | 0.01% | 0.02% | 0.01% | 0.01% |

From the results of all filters studied there is no indication of drug absorption on any filter membrane since the assay seems to be stable before and after filtration.

Although, Nylon, PES and PTFE filters seem not to be susceptible to increase the related substances level upon the filtration process, PVDF filter is selected and it will be used in the manufacturing process of the present invention.

In order to investigate the potential contamination of the tip during use, i.e. by accidently touching the human eye, a microbial challenge test has been performed. A challenge suspension containing *Brevundimonas Diminuta* was prepared. The dropper of the multi-dose PF system was actuated by immersing the tip into the challenge suspension and left at room temperature in order to simulate in use conditions.

The sterility of the optimized formulations was also checked upon storage in the multi-dose PF container for 6 months at 40° C. The results of these tests are presented in Table 25 below.

TABLE 25

Results of sterility tests for Latanoprost & Latanoprost-Timolol PF eye drops solution in the multi-dose PF container.

| Test | Requirements | Result |
|---|---|---|
| Sterility upon storage | | |
| Product at zero-time | Sterile | Conforms |
| Product after storage for 6 months at 40° C. | Sterile | Conforms |
| In use sterility test | | |
| Product at zero-time | Sterile | Conforms |
| Product after in-use test | Sterile | Conforms |
| In use sterility challenge test | | |
| Product at zero-time | Sterile | Conforms |
| Product after challenging and incubation | Sterile | Conforms |

It is obvious that the multi-dose PF container meets the sterility requirements for Latanoprost & Latanoprost-Timolol PF eye drops solution.

The preferred compositions according to the present invention are presented in tables 26 & 27 below.

TABLE 26

Preferred compositions of Latanoprost PF eye drops solution

| Ingredients | % w/v | | |
|---|---|---|---|
| Latanoprost | 0.005 | 0.005 | 0.005 |
| Cremophor RH-40 or Cremophor EL | 1.500-5.000 | 1.500-5.000 | 2.500 |
| Poloxamer 407 | — | 1.500-3.000 | — |
| Disodium edetate dehydrate | — | — | 0.111 |
| NaCl | 0.350-0.500 | 0.250-0.400 | 0.370 |
| NaH$_2$PO$_4$•2H$_2$O | 0.600-0.950 | 0.600-0.950 | 0.900 |
| Na$_2$HPO$_4$ | 0.100-0.200 | 0.100-0.200 | 0.130 |
| NaOH/HCl 1N | q.s pH 6.00 | | |
| Water for injections | q.s 100.0 | | |

TABLE 27

Preferred compositions of Latanoprost-Timolol PF eye drops solution

| Ingredients | % w/v | | |
|---|---|---|---|
| Latanoprost | 0.005 | 0.005 | 0.005 |
| Timolol | 0.500 | 0.500 | 0.500 |
| Timolol Maleate | 0.683 | 0.683 | 0.683 |
| Cremophor RH-40 or Cremophor EL | 1.500-5.000 | 1.500-5.000 | 2.500 |

TABLE 27-continued

Preferred compositions of Latanoprost-Timolol PF eye drops solution

| Ingredients | % w/v | | |
|---|---|---|---|
| Poloxamer 407 | — | 1.500-3.000 | — |
| Disodium edetate dehydrate | — | — | 0.111 |
| NaCl | 0.300-0.450 | 0.300-0.400 | 0.360 |
| NaH$_2$PO$_4$•2H$_2$O | 0.650-0.800 | 0.600-0.750 | 0.800 |
| Na$_2$HPO$_4$ | 0.250-0.350 | 0.200-0.300 | 0.250 |
| NaOH/HCl 1N | q.s pH 6.00 | | |
| Water for injections | q.s 100.0 | | |

While the present invention has been described with respect to the particular embodiment, it will be apparent to those skilled in the art that various changes and modifications may be made in the invention without departing from the spirit and the scope thereof, as defined in the claims.

The invention claimed is:

1. A preservative-free ophthalmic pharmaceutical composition consisting of:
   Latanoprost or a combination of Latanoprost and Timolol;
   at least one Latanoprost solubilizing agent having an hydrophilic-lipophilic balance (HLB) value >10 selected from the group consisting of polyoxyl 40 hydrogenated castor oil, polyoxyl 35, castor oil poloxamer 407, and mixtures thereof, wherein said solubilizing agent is present in the composition in an amount from 1.5% to 5% w/v;
   at least one buffering agent selected from the group consisting of sodium dihydrogen phosphate dihydrate, anhydrous disodium phosphate, and mixtures thereof;
   at least one tonicity agent which is sodium chloride;
   at least one chelating agent which is disodium edetate dehydrate,
   water, and
   optionally at least one pH adjusting agent;
   wherein Latanoprost is present in the composition in an amount of 0.005% w/v, wherein when present, Timolol is present in the composition in an amount of 0.500% w/v.

2. The preservative-free ophthalmic pharmaceutical composition according to claim 1, wherein the amount of polyoxyl 40 hydrogenated castor oil in the composition is from 1.5% to 5% w/v, if present, the amount of polyoxyl 35 castor oil in the composition is from 1.5% to 5% w/v, if present, and the amount of poloxamer 407 in the composition is from 1.5% to 3% w/v, if present.

3. The preservative-free ophthalmic pharmaceutical composition according to claim 1, wherein the amount of sodium chloride in the composition is from 0.25% to 0.50% w/v.

4. The preservative-free ophthalmic pharmaceutical composition according to claim 1, wherein the amount of disodium edetate dehydrate in the composition is up to 0.15% w/v.

5. The preservative-free ophthalmic pharmaceutical composition according to claim 1, wherein the pH value of the composition is between 5.8 and 6.2.

6. The preservative-free ophthalmic pharmaceutical composition according to claim 1, wherein the composition has been sterilized under filtration with hydrophilic modified PVDF membrane.

7. The preservative-free ophthalmic pharmaceutical composition according to claim 1, wherein the composition is in a container equipped with an integral bacterial protection system.

8. The preservative-free ophthalmic pharmaceutical composition according to claim 1, wherein said solubilizing agent is present in the composition in an amount from 2.5% to 5% w/v.

9. A preservative-free ophthalmic pharmaceutical composition consisting of one of the following:

| Ingredients | % w/v | | |
|---|---|---|---|
| Latanoprost | 0.005 | 0.005 | 0.005 |
| Timolol | 0.500 | 0.500 | 0.500 |
| Timolol Maleate | 0.683 | 0.683 | 0.683 |
| polyoxyl 40 hydrogenated castor oil or polyoxyl 35 castor oil | 1,.00-5.000 | 1.500-5.000 | 2.500 |
| Poloxamer 407 | — | 1.500-3.000 | — |
| Disodium edetate dehydrate | — | — | 0.111 |
| NaCl | 0.300-0.450 | 0.300-0.400 | 0.360 |
| $NaH_2PO_4 \cdot 2H_2O$ | 0.650-0.800 | 0.600-0.750 | 0.800 |
| $Na_2HPO_4$ | 0.250-0.350 | 0.200-0.300 | 0.250 |
| NaOH/HCl 1N | q.s pH 6.00 | | |
| Water for injections | q.s 100. | | |

10. The preservative-free ophthalmic pharmaceutical composition according to claim 1, wherein the composition is in a container equipped with a dispensing tip having an inner diameter and an outer diameter, wherein the ratio of the inner diameter to the outer diameter of the dispensing tip is from 1:1 to 1:6.

11. The preservative-free ophthalmic pharmaceutical composition according to claim 1, wherein the composition does not contain Timolol.

12. A preservative-free ophthalmic pharmaceutical composition consisting of one of the following:

| Ingredients | % w/v | | |
|---|---|---|---|
| Latanoprost | 0.005 | 0.005 | 0.005 |
| polyoxyl 40 hydrogenated castor oil or polyoxyl 35 castor oil | 1.500-5.000 | 1.500-5.000 | 2.500 |
| Poloxamer 407 | — | 1.500-3.000 | — |
| Disodium edetate dehydrate | — | — | 0.111 |
| NaCl | 0.350-0.500 | 0.250-0.400 | 0.370 |
| $NaH_2PO_4 \cdot 2H_2O$ | 0.600-0.950 | 0.600-0.950 | 0.900 |
| $Na_2HPO_4$ | 0.100-0.200 | 0.100-0.200 | 0.130 |
| NaOH/HCl 1N | q.s pH 6.00 | | |
| Water for injections | q.s 100. | | |

13. The preservative-free ophthalmic pharmaceutical composition according to claim 1, wherein the composition has a viscosity of 1.34 to 1.66 centipoise.

* * * * *